United States Patent [19]

McDevitt

[11] 4,166,391
[45] Sep. 4, 1979

[54] MOLTEN METAL SAMPLER

[76] Inventor: Robert F. McDevitt, Box 551, Ogden Dunes, Portage, Ind. 46368

[21] Appl. No.: 907,110

[22] Filed: May 18, 1978

Related U.S. Application Data

[63] Continuation-in-part of Ser. No. 768,711, Feb. 15, 1977, abandoned, which is a continuation-in-part of Ser. No. 720,697, Sep. 7, 1976, Pat. No. 4,112,772, which is a continuation of Ser. No. 565,396, Apr. 7, 1975, abandoned.

[51] Int. Cl.² .............................................. G01N 1/12
[52] U.S. Cl. ............................................. 73/425.4 R
[58] Field of Search .................. 73/421.5 R, DIG. 9

[56] References Cited

U.S. PATENT DOCUMENTS

| | | | |
|---|---|---|---|
| 2,281,220 | 4/1942 | Anderson | 403/205 |
| 3,357,250 | 12/1967 | Lowdermilk | 73/DIG. 9 |
| 3,686,949 | 1/1971 | Hackett | 73/DIG. 9 |
| 3,751,986 | 8/1973 | Boron | 73/DIG. 9 |
| 3,859,857 | 1/1975 | Falk | 73/DIG. 9 |
| 3,994,172 | 11/1976 | Kelsey | 73/DIG. 9 |

FOREIGN PATENT DOCUMENTS 1559045  1/1969  France ................................. 73/DIG. 9

*Primary Examiner*—S. Clement Swisher

[57] ABSTRACT

The invention involves a connector attachable to a lance for detachably connecting a molten metal sampler or device thereto. More particularly, the purpose of the invention is to provide a safe and simple method whereby a cast sample for example, through use of an improved connector may be obtained from a flowing metal stream when molten metal is being transferred by pouring from one type vessel to another. The sample may be used directly for spectographic analysis or can be drilled to provide a sample for wet chemical analysis. In addition, the sample may be sawed and polished for use in metallographic study of grain structure, cleanliness, etc. The entire sample can be cast in a two piece mold assembly made of a material with optimum cooling venting and dimensional characteristics.

23 Claims, 7 Drawing Figures

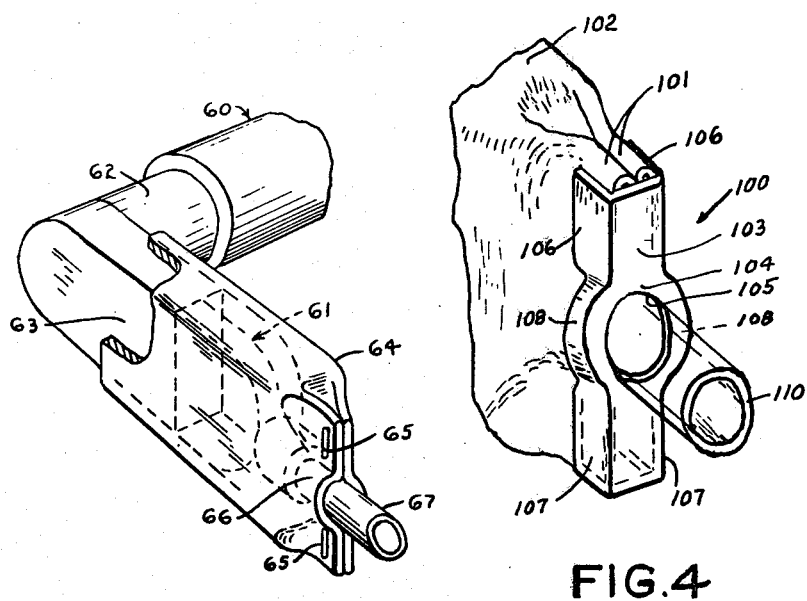
FIG.1
FIG.4
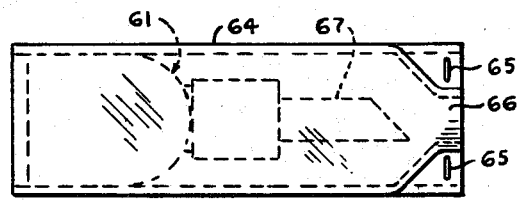
FIG.2
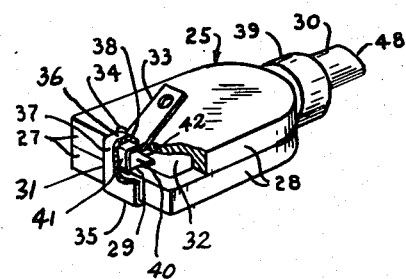
FIG.3

MOLTEN METAL SAMPLER

This application is a continuation-in-part of my abandoned application Ser. No. 768,711 filed Feb. 15, 1977, the latter is a continuation-in-part of application Ser. No. 720,697 filed Sept. 7, 1976 and now U.S. Pat. No. 4,112,772; the latter is continuation of abandoned application Ser. No. 565,396 filed Apr. 7, 1975.

In the processing of metals in the molten state it is necessary to obtain a sample representative of the parent material, at various stages in the processing, for the evaluation of either its chemical composition or metallographic structure.

The device or sampler, adapted for attachment to the connector embodying the subject invention, is preferably designed to obtain a quick chilled sample from the flowing metal as it is transferred by pouring from one type vessel to another. It is primarily designed to be used where molten steel is poured from a teeming ladle into a mold.

For many years the typical method of sampling molten metal in the steel industry was to use what was defined as a spoon. The spoon consisted of a deep bowl type ladle or sampler attached to the end of a long handle and made of either cast or forged steel. The spoon varied in size and had a lip to facilitate pouring. In practice the pouring stream was controlled to a slow or partial stream and the spoon was then dipped into the stream of metal to obtain the sample. The spoon was usually tipped into either the right or left side of the stream, whichever was most convenient, and partially filled with molten metal. The molten metal content of the spoon was then poured into a small test mold positioned on the platform. The casting from this mold provided a sample 4" to 8" long, tapered, and 1" to 2" square in cross-section.

This conventional method of sampling is not only wasteful from the standpoint of time and material but also exposes the molten metal to atmospheric oxygen which can cause variations in the chemical content of the sample. The degree of the chemical variation is dependent on the grade of steel as well as the techniques of the individual doing the sampling. The effect is pronounced with the elements of carbon and manganese with varying effects on other elements. Although the steel industry has been aware of the phenomenon and does make corrections; much could be gained by minimizing this condition. Other disadvantages of this conventional method are the need to arrest the stream and the extreme safety hazards involved with taking a sample when the molten metal stream cannot be controlled.

Advantages of the invention or inventions over the spoon technique are:
1. Minimum exposure of the sample to atmospheric oxygen.
2. Simplified sampling technique eliminating the heavy spoon and repouring technique.
3. Elimination of the need to arrest the molten metal stream flow.
4. Precision cast samples with a quick chill and tailored for minimum preparation.
5. Representative and reproducible results at a minimum of expense.
6. Safe procedure in obtaining samples.

A significant objective of the invention is to provide a sampler embodying improved principles of design and construction and particularly with respect to the fore extremity of the structure.

In view of the foregoing, one of the important objects of the invention is to provide a connector for use with an elongated device for obtaining a sample of a liquid, such as molten metal, which device may comprise, among other things, a pair of half sections forming a chamber, tubular means which has an inner extremity communicatively connected to the chamber and an outer extremity provided with an entrance for initially receiving molten metal for flow into the chamber, means at one extremity of the device for holding the sections together, and means at its opposite extremity for holding the sections and tubular means assembled, and wherein one or both of these holding means may serve to facilitate disassembly of the sections. More particularly in this respect, one of the holding means for the sections comprises clip means, and an appendage held in place by this clip means may be utilized for indentificating purposes and effect release of the clip means, and the means for holding the sections and tubular means may be operated to facilitate disassembly of these components.

Further, each section of the device may include a relatively large head portion provided with a recess and an extended portion having a center groove therein so that when the sections are correctly assembled the recesses will form a primary chamber and the grooved extensions will form a tubular formation communicating with the chamber.

An important object of the subject invention is to provide a connector which is attachable to a lance and serves to detachably support a device therein in various longitudinal positions.

More particularly, the connector is in the form of an elongated housing having an end wall structure provided with an opening so that a device can be stored in a retracted or inoperative position in the housing or be shifted to an operative position so that at least a portion of the tubular means of the device can be extended through the opening for use and entry into molten metal.

Specific objects of the invention reside in providing a connector which is preferably constructed of a suitable disposable material, such as pasteboard, and the above mentioned end wall structure serves to support the tubular means during the period a sample is being obtained.

Also, an object is to provide fastening means, in the form of clip means or staple means for securing portions of the housing whereby to assist in forming the end wall structure above referred to and an improved deoxidizing element operatively associated therewith.

Additional objects and advantages of the invention reside in providing a connector which is safe and efficient to use, and one which can be economically manufactured on a production basis.

Other objects and advantages will become apparent after the description hereinafter set forth is considered in conjunction with the drawings annexed hereto.

In the drawings:

FIG. 1 is a perspective view of connector supporting a molten metal sampler and a lance attached to the connector;

FIG. 2 is a side view of the connector and device shown in FIG. 1;

FIG. 3 is a perspective view of a sampler which can be utilized with the lance and connector shown in FIG. 2;

FIG. 4 is a perspective view of a way to secure portions of the housing together;

Figure 5:
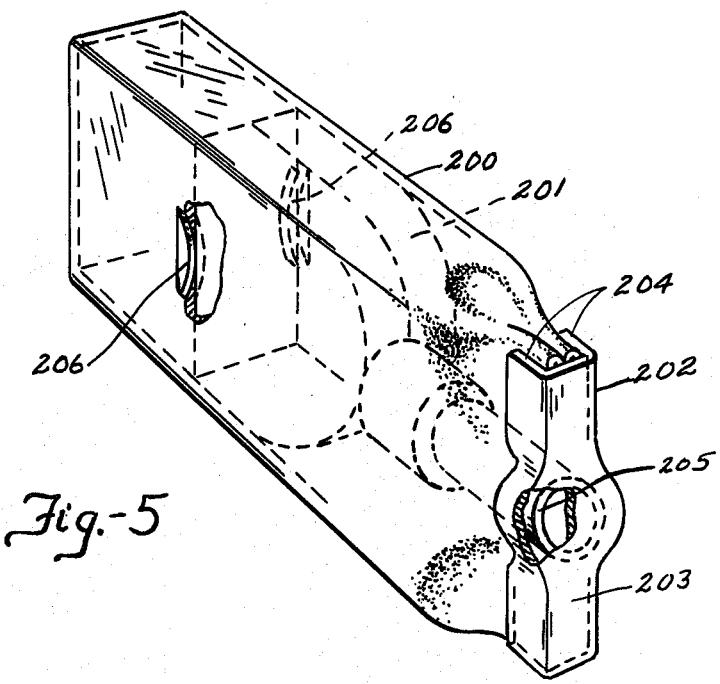
FIG. 5 is a perspective view of another modified structure.

Referring to FIG. 1 there is disclosed a lance generally designated 60 and a device 61, which may be constructed as illustrated in FIG. 3, of the drawing, and a connector 64.

More particularly, FIG. 1 shows the lance provided with a generally L-shaped adapter or fitting having a cylindrical portion 62 which is telescopically tightly fitted into an end of the lance and an offset 63, generally rectangular in cross-section, for slidable reception in an open end of the connector 64 which is generally in the form of a rectangular housing which contains the device and serves to protect it as described hereinafter. The opposite end of the housing is crimped, folded or formed so that portions thereof are secured together by staples 65, or equivalent means, to provide a tubular formation 66 through which a tubular means 67 of the device may be inserted for support as depicted in FIG. 1. This unique organization affords a setup whereby the device may be shifted from a dotted line inoperative or storage position as in FIG. 2 or to an operative position with the tubular means 67 extended through the tubular formation 66 for use. This organization also serves to protect the device when introduced into a stream or mass of molten metal to obtain a sample and assist in preventing contamination of the sample obtained.

As stated above the device 61 may be like the device shown in FIG. 3. The device 25 in FIG. 3 may comprise half sections 28 having end portions provided with notches 29 (one shown) which form a generally rectangular opening axially aligned with the longitudinal axis of a tubular receiving means 30 and through which extends a sheet metal appendage 31, preferably rectangular in cross-section, so that an inner portion of the appendage is located in a chamber 32 formed by the head portions 28 of the sections and an outer portion 33 provided with an aperture is located exteriorly of the head portions to which a tab may be attached for identification purposes. The notches 29 are similar to those identified as 234 in FIGS. 17 and 18 of the above identified continuation application. The outer planar side surfaces of the head portions 28 adjacent to the notches 29 are preferably respectively provided with transversely disposed corresponding grooves 34 (one shown) so that resiliently flexible clip means 35 having legs 36 joined by a bridge 37 embrace portions of the head portions and so that detents 38 formed on the ends of the legs may be manually located or snapped in the grooves 34. This clip means serves to hold the head portions together at one extremity of the device and a sleeve or casing 39 serves to hold the channel or extended portions at the other extremity of the device together and about the tubular means 30. The clip means also serves to cause a portion 40 of the appendage 31 to be locked in the notches 29, a portion 41 to be locked between the sections and the clip means, and an indented portion 42 of the appendage in one of the grooves 34. This appendage and clip means are substantially the same as those shown in FIG. 15 of said continuation application. The free outer portion 31 not only serves as a means whereby identification means may be attached thereto but is a handle which can be manually grasped or pulled by a tool whereby to release the clip means from the half sections. Obviously, the appendage per se may serve as an identification means.

In view of the foregoing it should be manifest that the design and construction of the device for use with the connector 64 may be in different forms or shapes, provided it can be manipulated to a retracted or inoperative position as depicted in FIG. 2 or to an extended operation position so that its tubular means 67 is extended for support in the tubular formation 66 for use. This formation is formed in what may be defined as end wall structure of the connector.

Referring to FIG. 4 of the drawing there is shown a perspective view of a portion of a sampling device which substantially corresponds to the one depicted in FIG. 1 except that a fastening means, preferably in the form of a clip means generally designated 100 is utilized to hold frontal folded or bent portions 101 of a connector or housing 102 together in lieu of the staples or fastening means shown in FIG. 3.

More specifically in this respect, the clip means preferably comprises a metal generally channel or U-shaped member having a base wall 103 which is formed to provide a generally enlarged central portion 104 having a circular opening 105 therein and side walls having two pairs of substantially parallel portions 106 and 107 which are joined together by curved intermediate portions 108. The curved portions assist in holding portions of the housing to form a generally tubular formation of an end wall structure for receiving an inner extremity of an entrance tube 110. This tube extends through the opening 105 and its outer extremity serves to initially receive the molten material. The cross-dimensional tolerances between the tubular formation, tube 110 and opening 105 are preferably predetermined to provide relatively close fits and the same is substantially true with respect to the general overall thickness of the folded frontal portions 101 and the dimensions between the pairs of portions 106 and 107. The portions 106 and 107 may be of a resiliently flexible character so that the clip means may be readily fastened in place by manipulation or they may be pressed into place by any suitable mechanical means.

This clip means serves several purposes, such as protecting the frontal portions of the connector, preventing any possible entry of molten material into the connector and for reinforcing or stabilizing the operative position of the entrance tube 110. The fastening means may also serve to assist in holding the tube in the end formation as well as maintain the stability of the latter. If found desirable, a quantity of refractory cement may be placed about the tube 110 at the opening 105 to prevent any flow of the molten material through the opening.

The connector 100 or casing 102 is preferably constructed of a desirable frangible material such as pasteboard.

A modified structure or sampler is exemplified in FIG. 5 of the drawing. It is quite similar to the device shown in FIG. 4 and includes an outer rectangular housing or casing 200 and a sampler or device 201 is arranged in the front extremity of the casing. This front extremity is preferably constructed by deforming or otherwise shaping the frontal wall portions of the casing to form a generally central tubular formation like the formation 66 in FIG. 2 and a fastening means 202 serves to hold or lock the frontal wall portions in place.

The fastening means 202 may be designed and constructed in various ways but is preferably generally channel in shape and has a front wall 203 and side walls 204 which forcibly engage or embrace the frontal walls of the casing. The front wall 203 is not interrupted by an opening as shown in FIG. 4 and an entrance tube 205 of the device extends into the tubular formation for stabilizing and engages or abuts against the front wall of 203 and limits forward movement of the device. Any means suitable for the purpose may be utilized to limit rear movement of the device in the casing, such as, for example, by indenting portions of the casing as indented at 206 for engagement by a rear enlarged portion or head of the device.

The modified structure, among other things, serves to firmly locate and protect the sampler in the casing and the front wall of the fastening means serves to prevent entry of slag into the entrance tube as it is being projected into molten metal. The structural character of the fastening means are such that the foregoing may be readily accomplished.

Figure 6:
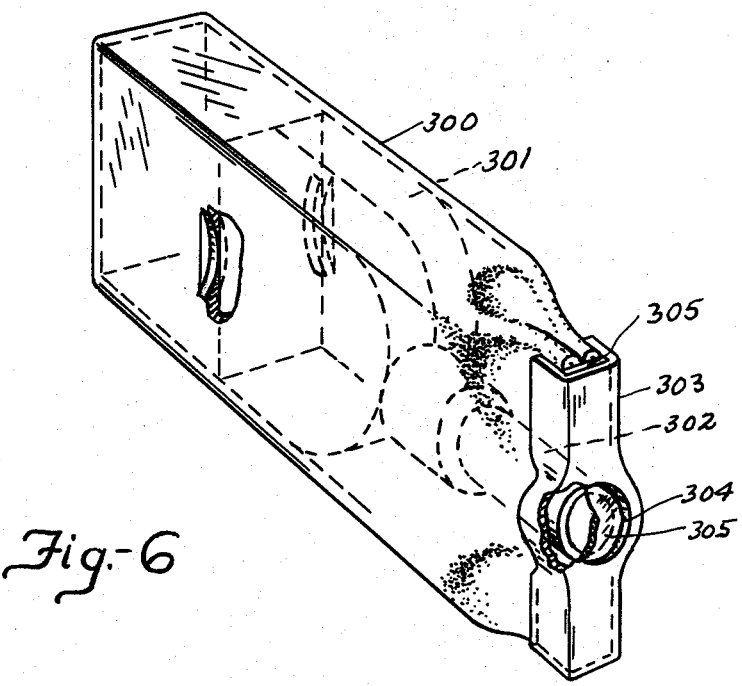
FIG. 6 is a perspective view of an additional modified structure.

Another modified structure is disclosed in FIG. 6, which is also similar to the structures of FIGS. 4 and 5 and includes a casing 300, a sampler 301 having an entrance tube 302 and a fastening means 303 provided with a central opening 304. The improvement in FIG. 6 primarily comprises locating or interposing a deoxidizing element 305 between the fore end of the tube 302 and the front wall of the fastening means to normally close the opening 304. Due to the structural character and location of the fastening means 303 and those shown in FIGS. 4 and 5, the front extremity of the casing is stabilized and protected sufficiently to allow introduction of the structure into a supply of molten material so that a satisfactory sample of the material substantially free of contamination can be readily obtained.

Figure 7:
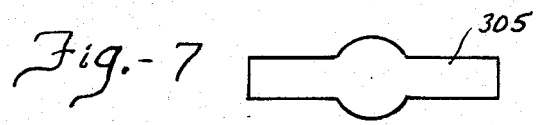
FIG. 7 is a plan view of an improved deoxidizing element utilized in connection with the structure of FIG. 6.

The deoxidizing element 305 may be constructed of aluminum or any other element suitable for the purpose of conditioning various kinds of molten materials. The element 305 is preferably elongated, in the form of a planar relatively than rectangular strip which is enlarged intermediate its extremities as illustrated in FIG. 7 in order to cover the opening 304.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. An elongated casing having one extremity formed to provide end wall structure providing a relatively small center tubular formation and an opposite open extremity for accommodating an elongated sampling device having an extended tubular entrance in a manner whereby the device can be moved in the casing to locate the entrance through the formation for use.

2. The casing defined in claim 1, in which at least one cross-dimension of the casing is such that the device is frictionally held in any position to which it is adjusted therein.

3. The casing defined in claim 1, in which said casing is of a length somewhat greater than the device so the latter can be substantially confined therein in an inoperative position.

4. The casing defined in claim 1, in which the open extremity of the casing may be utilized to accommodate an end of a lance whereby to facilitate holding the device in a position of use and manipulation of the casing and a device as a composite unit.

5. In combination: a connector constructed of pasteboard, said connector being in the form of an elongated housing having one open end and an opposite extremity which has deformed portions forming a tubular formation, and a molten metal sampler disposed in said housing for manipulation to an inoperative position substantially within its confines or to a position whereby a tubular entrance provided on said sampler can be extended through said tubular formation for use.

6. The combination defined in claim 5, including a fitting having a first portion disposed in said open end and a second portion offset from said first portion.

7. A connector for the purpose described comprising a casing constructed of a frangible material and formed to provide a generally tubular end formation and adjacent frontal edge portions, means for receiving a molten material disposed in said casing, an entrance tube having an inner extremity extending through said end formation and into said receiving means and an exposed outer extremity for initially receiving a molten material for flow into said receiving means, and means for fastening said frontal edge portions of said casing in a relationship whereby to assist in maintaining the stability of said end formation for reception of said inner extremity of said tube.

8. The connector defined in claim 7, in which said fastening means also assists in holding the tube in an operative position.

9. The connector defined in claim 7, in which said fastening means is in the form of means extending through said edge portions.

10. The connector defined in claim 7, in which said fastening means is in the form of clip means which embraces said edge portions and has an opening through which said tube extends.

11. A subassembly for accommodating a device having a chamber and an entrance tube for receiving a molten material, said subassembly comprising a casing formed to provide frontal edge portions and a central tubular end formation for receiving the tube, and means for fastening said edge portions in a predetermined relationship.

12. The subassembly defined in claim 11, in which said fastening means is generally in the form of a channel which has portions embracing said edge portions and a central opening through such a tube may be extended.

13. A fastening means for a casing having a central tubular formation and adjacent frontal edge portions, said fastening means having portions for embracing such edge portions and a central opening for accommodating an entrance tube for receiving a molten material for flow into a receiving means adapted for disposition in such a casing.

14. An elongated casing having a fore hollow extremity for accommodating an elongated sampling device having an extended tubular entrance, and said extremity having end wall structure providing a tubular formation into which the tubular entrance may be located for use.

15. The casing defined in claim 14, including a member connected to said casing for closing said tubular entrance.

16. The casing defined in claim 14, including a member connected to said casing for closing said tubular entrance, and a deoxidizing element interposed between said member and said tubular entrance.

17. The casing defined in claim 14, including a deoxidizing element located at said entrance, and means for holding said element in place.

18. A subassembly for accommodating a device having a chamber and a tube having an entrance for receiving a molten material, said subassembly comprising a non-metallic casing formed to provide frontal end wall structure having a tubular formation for receiving the tube, and means connected to said subassembly for closing said tubular formation.

19. The subassembly defined in claim 18, including deoxidizing means held at the entrance of said tube.

20. The subassembly defined in claim 18, in which said end wall structure comprises deformed portions of said casing, and said casing means also serves to hold said deformed portions together.

21. The subassembly defined in claim 18, in which said closing means has an opening, and an element is interposed between said closing means and said entrance.

22. The subassembly defined in claim 18, in which said casing is provided with means whereby to assist in holding such a device therein.

23. In combination: a connector constructed of a non-metallic material, said connector being in the form of an elongated casing having a frontal end wall structure provided with a tubular formation which are constructed by shaping portions of said casing, an elongated molten metal sample disposed in said casing and having a tubular entrance disposed in said tubular formation for receiving molten material, means at said end wall structure for limiting forward movement of said device, and means provided on said casing spaced rearwardly of said limiting means serving to limit rear movement of said device.

* * * * *